United States Patent [19]
Choi et al.

[11] Patent Number: 5,955,499
[45] Date of Patent: *Sep. 21, 1999

[54] PHENYLALKYLAMINOALCOHOL CARBAMATES AND PROCESS FOR PREPARING THE SAME

[75] Inventors: Yong Moon Choi, Towaco, N.J.; Jai Kook Byun, Seoul, Rep. of Korea

[73] Assignee: Yukong Limited, Seoul, Rep. of Korea

[ * ] Notice: This patent is subject to a terminal disclaimer.

[21] Appl. No.: 08/619,657
[22] PCT Filed: Sep. 6, 1995
[86] PCT No.: PCT/KR95/00114
  § 371 Date: Jul. 1, 1996
  § 102(e) Date: Jul. 1, 1996
[87] PCT Pub. No.: WO96/07637
  PCT Pub. Date: Mar. 14, 1996

[30] Foreign Application Priority Data

Sep. 9, 1994 [KR] Rep. of Korea .................. 94-22798

[51] Int. Cl.⁶ .................................................. A61K 31/27
[52] U.S. Cl. ........................................... 514/489; 560/163
[58] Field of Search .............................. 560/163; 514/489

Primary Examiner—Michael L. Shippen
Attorney, Agent, or Firm—Gibbons, Del Deo, Dolan, Griffinger & Vecchione

[57] ABSTRACT

O-carbamoyl-(D/L)-phenylalaninol represented by structural formula I is pharmaceutically useful to treat diseases of the central nervous system, which is prepared by a characteristic process comprising the steps of: treating phenylalaninol with benzyl chloroformate in a basic aqueous solution medium, to give N-benzyloxycarbonyl-phenylalaninol; subjecting this intermediate to reaction with phosgene and then, to the treatment with excess of concentrated ammonium hydroxide aqueous solution, to provide O-carbamoyl-N-benzyloxycarbonyl-phenylalaninol; deprotecting it through hydrogenolysis reaction.

(I)

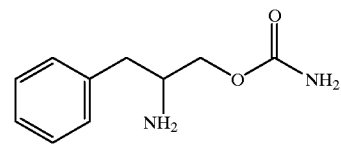

10 Claims, No Drawings

PHENYLALKYLAMINOALCOHOL CARBAMATES AND PROCESS FOR PREPARING THE SAME

BACKGROUND OF THE INVENTION

1. Field of the Invention

The present invention relates, in general, to pharmaceutically novel and useful organic compounds and, more particularly, to O-carbamoylphenylalaninol compounds including their racemates and enantiomers and the pharmaceutically acceptable salts thereof, useful to treat the diseases of the central nervous system, especially for depression. Also, the present invention is concerned with a process for preparing the same.

2. Description of the Prior Art

Organic alkyl carbamates have been effectively used for controlling various central nervous system (CNS) disorders. For example, U.S. Pat. Nos. 2,884,444, 2,937,119 and 3,313,697 disclose function of carbamate in CNS disorders, especially as antiepileptic and centrally acting muscle relaxant.

Phenylethylamine derivatives, one important class of therapeutical medicines useful for managing CNS diseases, have been used mainly to treat obesity, narcolepsy, minimal brain dysfunction and mild depression.

Recent design of pharmacologically useful compounds has been based on amino acids or the derivatives thereof, which is mainly attributable to the fact that many of the compounds found in biological systems come from amino acids or the derivatives thereof. In addition, in most cases, the function of a pharmaceutically useful compound is effected after it binds to an enzyme or receptor, which may trigger the regulatory mechanisms of the enzyme or receptor.

SUMMARY OF THE INVENTION

As a result of intensive and thorough research, the present inventors found that O-carbamoyl derivatives from (D/L)-phenylalaninol, (D)-phenylalaninol and (L)-phenylalaninol are pharmaceutically useful for CNS disorders, especially for depression.

Accordingly, it is a principal object of the present invention to provide novel phenylalkylaminoalcohol carbamate compounds, represented by the following structural formulas I, II and III:

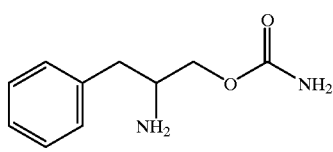
(I)

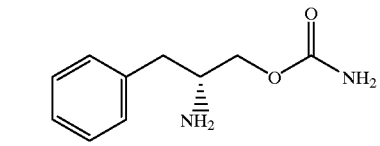
(II)

(III)

and pharmaceutically acceptable salts thereof.

It is another object of the present invention to provide a method for preparing the O-carbamoyl derivatives from (D/L)-phenylalaninol, (D)-phenylalaninol and (L)-phenylalaninol, represented by the structural formulas I, II and III.

DETAILED DESCRIPTION OF THE INVENTION

By virtue of the basic nitrogen atom, the novel compounds of the present invention form into pharmaceutically acceptable acid addition salts with organic or inorganic acids. Concrete examples of the acids suitable for the formation of pharmaceutically acceptable salts include hydrochloric, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic and the like. Additional acids can refer to "Pharmaceutical Salts", J. Pharm. Sci., 1977; 66(1): 1–19.

In accordance with the present invention, the compounds of Structural Formulas I, II and III are prepared as set forth in the following Reaction Schemes I, II and III, respectively. Following is of the preparation of the novel compounds in conjunction with the reaction schemes.

The compound of Structural Formula I is prepared as shown in Reaction Scheme I below.

REACTION SCHEME I

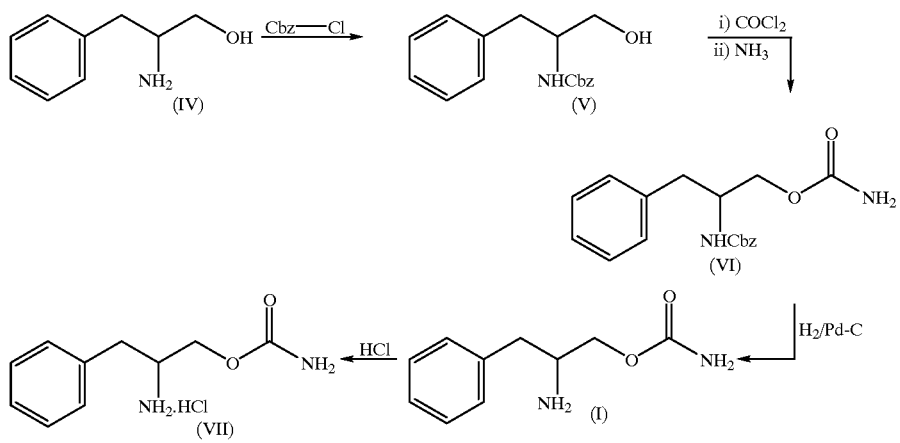

In Reaction Scheme I, first, phenylalaninol (IV) is converted to N-benzyloxycarbonylphenylalaninol (V) by reaction with benzyl chloroformate in a basic aqueous solution, which is subjected to carbamoylation with phosgene, followed by the ammonolysis with excess of concentrated ammonium hydroxide aqueous solation, to afford O-carbamoyl-N-benzyloxycarbonylphenylalaninol (VI). Removal of the benzyloxycarbonyl group, a nitrogen protecting group, by hydrogenolysis gives O-carbamoylphenylalaninol (I), which is, then, treated with ethereal hydrogen chloride provides O-carbamoylphenylalaninol hydrochloride salt (VII).

Details of the reaction conditions described in Reaction Scheme I is as follows. In the first step, the concentration of the starting material (IV) is between 0.1 and 3 molar and benzyl chloroformate is used at 1 to 2 equivalents. The basic aqueous solution has a pH value between 7 and 14 and the conversion reaction is carried out at temperatures ranging from −10 to 70° C.

For the conversion of compound (V) to (VI), 1 to 2 molar equivalent of phosgene, either neat or as solution in toluene, is used at 0.05 to 2 molar concentration of the compound (V). Halogenated alkane such as methylene chloride, ethereal solvents such as tetrahydrofuran, aromatic solvents such as toluene or the mixtures thereof can be used as a solvent. Use of a base as acid scavenger is recommended while the reaction can be completed in the absence of a base. Typically, a tertiary amine, such as triethylamine, diisopropylethylamine, triisopropylamine, DBU(1,6-diazabicyclo[5.4.0]undec-7-ene), DBN(1,5-diazabicyclo[4.3.0]non-5-ene), antipyrine and dimethylphenylamine, can be used for this purpose. The reacting ammonia can be used as neat or as solution in water or lower alkyl alcohol such as methanol, ethanol, n-propanol or isopropanol, and 1 to 1,000 molar equivalent is used. The reaction temperature is between −30 and 60° C.

As for the step of preparing compound (I) from (VI), an ethereal solvent such as THF, an alcoholic solvent such as methanol, water, an aromatic solvent such as toluene, benzene, or xylene, an ester solvent such as ethyl acetate or any compositional mixture thereof is used as the reaction medium, and the hydrogenation reaction is carried out at a temperature of −10 to 150° C. under a 1 to 100 atm hydrogen pressure in the presence of a catalyst such as palladium (0.1% to 10% on charcoal, alumina or other supporting materials), platinum, platinum oxide, rhodium, iridium or yttrium. Typical substrate concentration of compound (VI) is between 0.05 and 5 molar.

To prepare the salt (VII) from the free base (I), an ethereal solvent such as THF, an alcoholic solvent such as methanol, an ester solvent such as ethyl acetate, an aromatic solvent or any compositional mixture thereof can be used. For the precipitation, a nonpolar organic solvent is used, such as dialkyl ether where the alkyl typically represents a lower alkyl of C1 to C6, either straight or branched. The concentration of the substrate (I) in the initial solution is on the order of 0.05 to 5 molar.

The compound of Structural Formula II is prepared as shown in Reaction Scheme II below.

REACTION SCHEME II

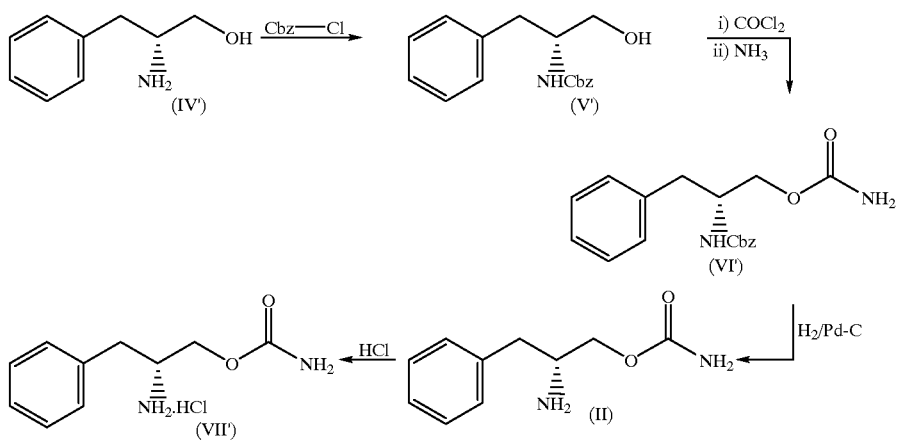

In Reaction Scheme II, (D)-phenylalaninol (IV') is converted to N-benzyloxycarbonylphenylalaninol (V') by reaction with benzyl chloroformate in a basic aqueous solution. Carbamoylation of compound (V') with phosgene followed by the ammonolysis of the chloroformate intermediate affords (D)-O-carbamoyl-N-benzyloxycarbonylphenylalaninol (VI'). Removal of benzyloxy-carbonyl group, a nitrogen protecting group, by hydrogenolysis gives (D)-O-carbamoylphenylalaninol (II). Treatment of compound (II) with ethereal hydrogen chloride provides (D)-O-carbamoylphenylalaninol hydrochloride salt (VII').

The reaction steps described in Reaction Scheme II are undertaken under the same conditions as those in Reaction Scheme I.

The compound of Structural Formula III is prepared as shown in Reaction Scheme III below.

REACTION SCHEME III

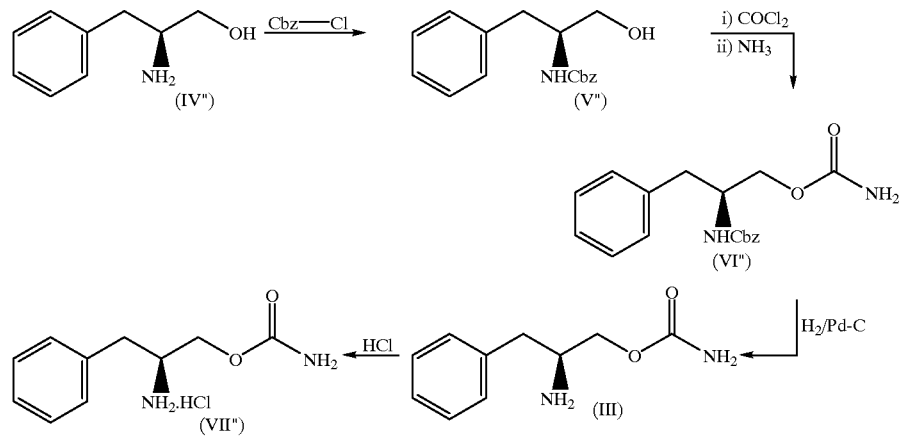

In Reaction Scheme III, first, (L)-phenylalaninol (IV") is converted through the reaction with benzyl chloroformate in a basic aqueous solution to N-benzyloxycarbonylphenylalaninol (V") which is subsequently subjected to carbamoylation with phosgene, followed by ammonolysis, to afford (L)-O-carbamoyl-N-benzyloxycarbonylphenylalaninol (VI"). Removal of the benzyloxycarbonyl group, a nitrogen protecting group, by hydrogenolysis gives (L)-O-carbamoylphenylalaninol (III), the treatment of which with ethereal hydrogen chloride provides (L)-O-carbamoylphenylalaninol hydrochloride salt (VII").

The reaction steps described in Reaction Scheme III are undertaken under the same conditions as those in Reaction Scheme I.

In therapeutic use as agents for various central nervous system (CNS) disorders, especially for depression, the compounds of the present invention are administered to patients at a dosage of from 0.7 to 7,000 mg per day. For a normal human adult with a body weight of approximately 70 kg, the administration amount is translated into a daily dose of 0.01 to 100 mg per kg of body weight. The specific dosage employed, however, may vary depending upon the requirements of the patient, the severity of patient's condition and the activity of the compound. The determination of optimum dosages for a particular situation is within the skill of the art.

In utilizing the compounds of the present invention for the central nervous system, particularly to treat depression, it is preferred to administer the compounds orally. Since the compounds absorb well orally, it usually will not be necessary to resort to parenteral administration. For oral administration, the present phenylalkylaminoalcohol carbamate compounds are preferably combined with a pharmaceutical carrier. The ratio of the carrier to the phenylalkylaminoalcohol carbamate compounds is not critical to express the effects of the medicine on the central nervous system, and they can vary considerably depending on whether the composition is to be filled into capsules or formed into tablets. In tableting, it is usually desirable to employ at least as much pharmaceutical carrier as the pharmaceutically active ingredients. Various edible pharmaceutical carriers or the mixture thereof can be used. A suitable carriers, for example, are a mixture of lactose, diabasic calcium phosphate and cornstarch. Other pharmaceutically acceptable ingredients can be further added, including lubricants such as magnesium stearate.

The therapeutic effect of the compounds according to the present invention in treating depression has been proved by "Forced Swimming Test", a well known pharmacological screening methods for depression and the results are shown in the following Table 1.

TABLE 1

| | (Oral administration in mice (1 hr)) | | |
|---|---|---|---|
| Treatment | Dose (mg/kg) | Immobility time (sec) (mean) | Inhibition (%) |
| Control | 0 | 132 | — |
| Compound II | 30 | 50 | 62 |
| Control | 0 | 105 | — |
| Compound III | 30 | 132.5 | n.s.* |
| Control | 0 | 154 | — |
| Compound I | 30 | 77 | 30 |

*n.s.: statistically not significant

As shown in Table 1, compound II exhibits the most potency against the forced swimming model for depression. Comound III, an optical antipode of compound II, showed no activity at 30 mg/kg dose level for this particular model. It is not surprising to find that compound I, which is the racemic mixture of compound II and compound III, has shown half the potency of the parmacologically active component, compound II.

A better understanding of the present invention may be obtained in light of following examples which are set forth to illustrate, but are not to be construed to limit, the present invention.

EXAMPLE I

Preparation of N-Benzyloxycarbonyl-D-phenylalaninol

In a 500 mL RB flask equipped with a mechanical stirrer and a dropping funnel, D-phenylalaninol (45.4 g, 300 mmol) was dissolved in 220 mL of distilled water, and cooled in an ice-bath. The pH of the solution was adjusted with 50% sodium hydroxide to 14. Benzyl chloroformate (49.3 mL, 345 mmol) was charged into the dropping funnel and added slowly to the well stirred solution over 0.5 hr. After the completion of the addition, the reaction mixture was stirred for 1 hr. at 0° C. The product precipitated from the reaction mixture as a white solid. It was collected by filtration and washed completely with distilled water. After being dried in vacuo, the solid thus obtained weighed 104 grams without any further purification: 99.8% Yield.

Melting point=90–92° C.

$[\alpha]_D^{20}$=+43.4 (c=1.0, EtOH)

Analysis calc.: C, 71.56; H, 6.71; N,4.91 Found: C, 71.35; H, 6.71; N,4.91

EXAMPLE II

Preparation of N-Benzyloxycarbonyl-D-phenylalaninol carbamate

In a 500 mL RB flask, N-benzyloxycarbonyl-D-phenylalaninol (13.56 g, 50 mmol) was charged with antipyrine (11.29 g, 60 mmol) in 250 mL of dry THF under a nitrogen atmosphere. The reaction mixture was cooled in an ice-bath and phosgene (30.3 mL of 1.93M solution in toluene, 58.5 mmol) was added quickly while vigorously stirring. After stirring for 1 hr., the formation of a corresponding chloroformate from the starting material was monitored by TLC. The chloroformate solution thus prepared, was slowly added to a well stirred and ice-chilled aqueous ammonium hydroxide solution (75 mL, 28–30%, 1,190 mmol) via cannula over 0.5 hr. The resulting reaction mixture was stirred for an extra 0.5 hr. The organic phase separated was collected. The aqueous phase was extracted twice with methylene chloride (100 mL). The combined organic phase was washed with brine (50 mL), dried over sodium sulfate, and concentrated to yield 17.8 g (113%) of foamy solid. It was purified a flash column chromatography to give 14.8 g of the title compound, white solid: 94% Yield.

Melting point=121–125° C.

$[\alpha]_D^{20}$=+28.6 (c=2.0, EtOH)

Analysis calc.: C, 65.84; H, 6.14; N, 8.53 Found: C, 66.68; H, 6.21; N, 7.80

EXAMPLE III

Preparation of D-Phenylalaninol carbamate hydrochloric acid salt

In a 160 mL Parr reactor, N-benzyloxycarbonyl-D-phenylalaninol carbamate (9.43 g) was added with 75 mL of anhydrous methanol and 10% palladium on charcoal (0.32 g). Then, the reactor was closed and purged with hydrogen for 1 min. The reaction was completed in 2 hrs. under 40 psi pressure of hydrogen at 45° C. The catalyst was filtered off. Thereafter, the organic layer was concentrated into 5.97 g (102%) of pale yellow thick liquid. The liquid was poured in 50 mL of anhydrous THF and cooled to 0° C. Anhydrous hydrogen chloride gas was then purged through the solution with slowly stirring for 0.5 hr. 50 mL of anhydrous ether was added, to give a precipitate. Filtration with THF-ether (1:1) mixture provided 6.1 g of the title compound as a white solid: 88% Yield.

Melting point=172–174° C.

$[\alpha]_D^{20}$=−12.9 (c=2.0, $H_2O$)

Analysis calc.: C, 52.60; H, 6.55; N, 12.14; Cl, 15.37 Found: C, 51.90; H, 6.60; N, 12.15; Cl, 15.52

EXAMPLE IV

Preparation of N-benzyloxycarbonyl-L-Phenylalaninol

The title compound was prepared in the same manner as that of Example I, except that (L)-phenylalaninol was used as the starting material.

Melting point=90–92° C.

$[\alpha]_D^{20}$=−42.0 (c=1.0, EtOH)

Analysis calc.: C, 71.56; H, 6.71; N,4.91 Found: C, 70.98; H, 6.67; N,4.95

EXAMPLE V

Preparation of N-benzyloxycarbonyl-L-Phenylalaninol carbamate

The title compound was prepared in the same manner as that of Example II, except that N-benzyloxycarbonyl-L-phenylalaninol was used as the starting material.

Melting point=121–128° C.

$[\alpha]_D^{20}$=−28.9 (c=2.0, EtOH)

Analysis calc.: C, 65.84; H, 6.14; N, 8.53 Found: C, 65.45; H, 6.15; N, 8.32

EXAMPLE VI

Preparation of L-Phenylalaninol carbamate hydrochloric acid salt

The title compound was prepared in the same manner as that of Example III, except that N-benzyloxycarbonyl-L-phenylalaninol carbamate was used as the starting material.

Melting point=175–177° C.

$[\alpha]_D^{20}$=+13.1 (c 1.0, H$_2$O)

Analysis calc.: C, 52.60; H, 6.55; N, 12.14; Cl, 15.37

Found: C, 51.95; H, 6.58; N, 12.09; Cl, 15.37

EXAMPLE VII

Preparation of N-benzyloxycarbonyl-D,L-Phenylalaninol

The title compound was prepared in the same manner as that of Example I, except that (D,L)-phenylalaninol was used as the starting material.

Melting point=72–75° C.

Analysis calc.: C, 71.56; H, 6.71; N,4.91 Found: C, 71.37; H, 6.74; N,4.84

EXAMPLE VIII

Preparation of N-benzyloxycarbonyl-D,L-Phenylalaninol carbamate

The title compound was prepared in the same manner as that of Example II, except that N-benzyloxycarbonyl-D,L-phenylalaninol was used as the starting material.

Melting point=130–133° C.

Analysis calc.: C, 65.84; H, 6.14; N, 8.53 Found: C, 65.85; H, 6.14; N, 8.49

EXAMPLE IX

Preparation of D,L-Phenylalaninol carbamate hydrochloric acid salt

The title compound was prepared in the same manner as that of Example III, except that N-benzyloxycarbonyl-D,L-phenylalaninol carbamate was used as the starting material.

Melting point=163–165° C.

Analysis calc.: C, 52.60; H, 6.55; N, 12.14; Cl, 15.37 Found: C, 51.92; H, 6.56; N, 11.95; Cl, 15.82

Other features, advantages and embodiments of the present invention disclosed herein will be readily apparent to those exercising ordinary skill after reading the foregoing disclosures. In this regard, while specific embodiments of the invention have been described in considerable detail, variations and modifications of these embodiments can be effected without departing from the spirit and scope of the invention as described and claimed.

What is claimed is:

1. O-Carbamoyl-(D/L)-phenylalaninol, represented by the following structural formula I:

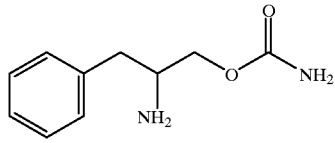

and the pharmaceutically acceptable salts thereof.

2. O-Carbamoyl-(D)-phenylalaninol, represented by the following structural formula II:

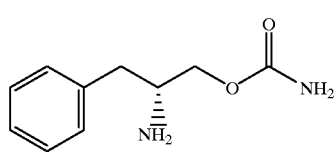

and the pharmaceutically acceptable salts thereof.

3. A process for preparing O-carbamoyl-(D/L)-phenylalaninol represented by the following structural formula I:

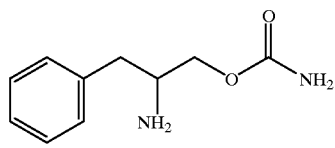

comprising the steps of:

treating (D/L)-phenylalaninol represented by the following structural formula IV:

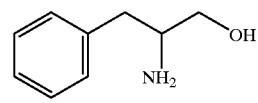

with benzyl chloroformate in a basic aqueous solution medium, to give N-benzyloxycarbonyl-(D/L)-phenylalaninol represented by the following structural formula V:

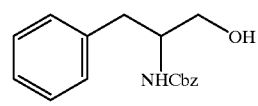

subjecting the compound of the structural formula V to reaction with phosgene and then, to the treatment with excess of concentrated ammonium hydroxide aqueous solution, to provide O-carbamoyl-N-benzyloxycarbonyl-(D/L)-phenylalaninol represented by the following structural formula VI:

(VI)

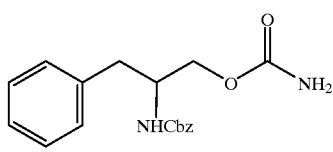

deprotecting the compound of the structural formula VI through hydrogenolysis reaction, to give O-carbamoyl-(D/L)-phenylalaninol represented by the structural formula I.

4. A process for preparing )-carbamoyl-(D)-phenylalaninol represented by the following structural formula II:

(II)

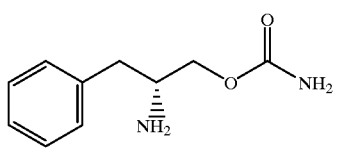

comprising the steps of:

treating (D)-phenylalaninol represented by the following structural formula IV':

(IV')

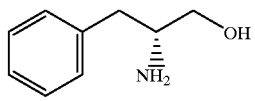

with benzyl chloroformate in a basic aqueous solution medium, to give N-benzyloxycarbonyl-(D)-phenylalaninol represented by the following structural formula V':

(V')

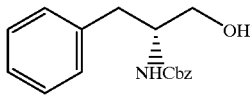

subjecting the compound of the structural formula V' to reaction with phosgene and then, to the treatment with excess of concentrated ammonium hydroxide aqueous solution, to provide O-carbamoyl-N-benzyloxycarbonyl-(D)-phenylalaninol represented by the following structural formula VI':

(VI')

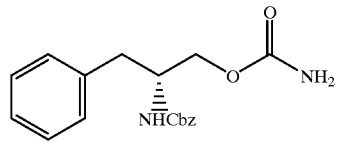

deprotecting the compound of the structural formula VI' through hydrogenolysis reaction, to give O-carbamoyl-(D)-phenylalaninol represented by the structural formula II.

5. A pharmaceutical composition which comprises as an active ingredient an anti-depressive effective amount of a compound of structural formula I as defined in claim 1 and a pharmaceutically acceptable carrier.

6. A pharmaceutical composition which comprises as an active ingredient an anti-depressive effective amount of a compound of structural formula II as defined in claim 2 and a pharmaceutically acceptable carrier.

7. A method for treating depression which comprises administering an anti-depressive effective amount of a compound of structural formula I as defined in claim 1 as an active ingredient to a mammal suffering from same.

8. A method for treating depression which comprises administering an anti-depressive effective amount of a compound of structural formula II as defined in claim 2 as an active ingredient to a mammal suffering from same.

9. A process for preparing the hydrochloride salt of O-carbamoyl-(D/L)-phenylalaninol represented by the following structural formula VII:

(VII)

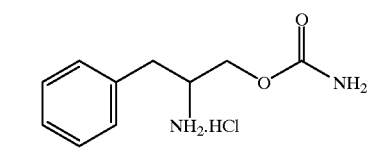

comprising the steps of:

treating (D/L)-phenylalaninol represented by the following structural formula IV:

(IV)

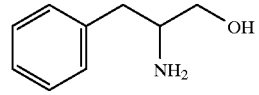

with benzyl chloroformate in a basic aqueous solution medium, to yield N-benzyloxycarbonyl-(D/L)-phenylalaninol represented by the following structural formula V:

(V)

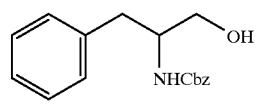

subjecting the compound of the structural formula V to reaction with phosgene and then to treatment with an excess of concentrated ammonium hydroxide aqueous solution to provide O-carbamoyl-N-benzyloxycarbonyl-(D/L)-phenylalaninol represented by the following structural formula VI:

(VI)

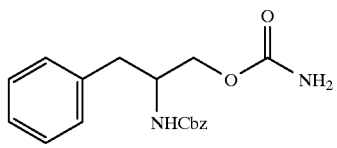

deprotecting the compound of the structural formula VI through hydrogenolysis reaction, to give O-carbamoyl-(D/L)-phenylalaninol represented by the structural formula I (I)

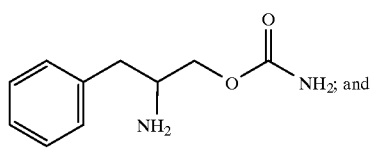

treating the compound of structural formula I with anhydrous hydrochloric acid in an ethereal solution to yield O-carbamoyl-(D/L)-phenylalaninol hydrochloric acid salt represented by structural formula VII, a pharmaceutically acceptable salt.

10. A process for preparing the hydrochloride salt of O-carbamoyl-(D)-phenylalaninol represented by the following structural formula VII'

(VII')

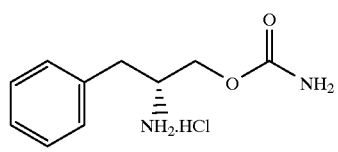

comprising the steps of:

treating (D)-phenylalaninol represented by the following structural formula IV':

(IV')

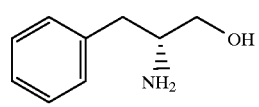

with benzyl chloroformate in a basic aqueous solution medium, to give N-benzyloxycarbonyl-(D)-phenylalaninol represented by the following structural formula V':

(V')

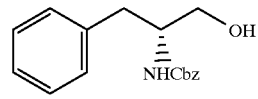

subjecting the compound of the structural formula V' to reaction with phosgene and then to treatment with an excess of concentrated ammonium hydroxide aqueous solution to provide O-carbamoyl-N-benzyloxycarbonyl-(D)-phenylalaninol represented by the following structural formula VI':

(VI')

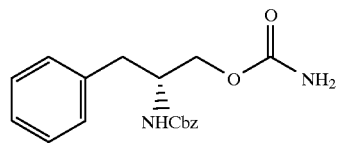

deprotecting the compound of the structural formula VI' through hydrogenolysis reaction, to give O-carbamoyl-(D)-phenylalaninol represented by the structural formula II:

(II)

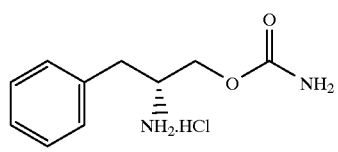

treating the compound of structural formula II' with anhydrous hydrochloric acid in an ethereal solution to give O-carbamoyl-(D)-phenylalaninol hydrochloric acid salt represented by structural formula VII', a pharmaceutically acceptable salt.

* * * * *